(12) United States Patent
Shuros et al.

(10) Patent No.: US 8,725,260 B2
(45) Date of Patent: May 13, 2014

(54) METHODS OF MONITORING HEMODYNAMIC STATUS FOR RHYTHM DISCRIMINATION WITHIN THE HEART

(75) Inventors: Allan C. Shuros, St. Paul, MN (US); Dan Li, Shoreview, MN (US); Quan Ni, Shoreview, MN (US)

(73) Assignee: Cardiac Pacemakers, Inc, St. Paul, MN (US)

( * ) Notice: Subject to any disclaimer, the term of this patent is extended or adjusted under 35 U.S.C. 154(b) by 855 days.

(21) Appl. No.: 12/366,334

(22) Filed: Feb. 5, 2009

(65) Prior Publication Data
US 2009/0204163 A1   Aug. 13, 2009

Related U.S. Application Data

(60) Provisional application No. 61/027,683, filed on Feb. 11, 2008.

(51) Int. Cl.
*A61N 1/00* (2006.01)

(52) U.S. Cl.
USPC .......................................................... 607/18

(58) Field of Classification Search
CPC .................................................. A61N 1/3627
USPC .......... 600/515, 516, 517, 518; 607/17, 18, 9, 607/14
See application file for complete search history.

(56) References Cited

U.S. PATENT DOCUMENTS

| | | |
|---|---|---|
| 3,310,885 A | 3/1967 | Alderson |
| 3,320,946 A | 5/1967 | Dethloff et al. |
| 3,536,836 A | 10/1970 | Pfeiffer |
| 3,568,661 A | 3/1971 | Franklin |
| 3,672,352 A | 6/1972 | Summers |
| 3,692,027 A | 9/1972 | Ellinwood |
| 3,757,770 A | 9/1973 | Brayshaw et al. |
| 3,794,840 A | 2/1974 | Scott |
| 3,943,915 A | 3/1976 | Severson |
| 4,003,379 A | 1/1977 | Ellinwood |

(Continued)

FOREIGN PATENT DOCUMENTS

| | | |
|---|---|---|
| EP | 0897690 | 2/1999 |
| EP | 0928598 | 7/1999 |

(Continued)

OTHER PUBLICATIONS

Garg et al., "Jugular Venous Pulse: An Appraisal", Journal, Indian Academy of Clinical Medicine, vol. 1, No. 3, Oct.-Dec. 2000, pp. 260-269.

(Continued)

*Primary Examiner* — Christopher D Koharski
*Assistant Examiner* — Nadia Ahmad
(74) *Attorney, Agent, or Firm* — Faegre Baker Daniels LLP

(57) ABSTRACT

Systems and methods of performing rhythm discrimination within a patient's body using sensed hemodynamic signals are disclosed. The method can include the steps of receiving an electrical activity signal from an electrode located within or near the heart, detecting an event of the heart based on the received electrical activity signal, sensing one or more mechanical measurements using a sensor located within the body, analyzing a mechanical activity signal received from the sensor, and confirming the type of event based on the mechanical and electrical activity signals. The sensor can comprise a single pressure sensor configured to sense both atrial and ventricular activity within the heart.

15 Claims, 7 Drawing Sheets

(56) References Cited

U.S. PATENT DOCUMENTS

| | | |
|---|---|---|
| 4,041,954 A | 8/1977 | Ohara |
| 4,127,110 A | 11/1978 | Bullara |
| 4,146,029 A | 3/1979 | Ellinwood |
| 4,223,801 A | 9/1980 | Carlson |
| 4,227,407 A | 10/1980 | Drost |
| 4,237,900 A | 12/1980 | Schulman et al. |
| 4,281,664 A | 8/1981 | Duggen |
| 4,360,019 A | 11/1982 | Portner et al. |
| 4,407,296 A | 10/1983 | Anderson |
| 4,450,527 A | 5/1984 | Sramek |
| 4,480,483 A | 11/1984 | McShane |
| 4,519,401 A | 5/1985 | Ko et al. |
| 4,541,431 A | 9/1985 | Ibrahim et al. |
| 4,543,955 A | 10/1985 | Schroeppel |
| 4,550,370 A | 10/1985 | Baker |
| 4,585,004 A | 4/1986 | Brownlee |
| 4,593,703 A | 6/1986 | Cosman |
| 4,600,855 A | 7/1986 | Strachan |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,680,957 A | 7/1987 | Dodd |
| 4,686,987 A | 8/1987 | Salo et al. |
| 4,697,595 A | 10/1987 | Breyer et al. |
| 4,719,921 A | 1/1988 | Chirife |
| 4,768,176 A | 8/1988 | Kehr et al. |
| 4,768,177 A | 8/1988 | Kehr et al. |
| 4,781,715 A | 11/1988 | Wurzel |
| 4,791,936 A | 12/1988 | Snell et al. |
| 4,793,825 A | 12/1988 | Benjamin et al. |
| 4,809,697 A | 3/1989 | Causey, III et al. |
| 4,845,503 A | 7/1989 | Adam et al. |
| 4,846,191 A | 7/1989 | Brockway et al. |
| 4,854,327 A | 8/1989 | Kunig |
| 4,899,752 A | 2/1990 | Cohen |
| 4,909,259 A | 3/1990 | Tehrani |
| 4,945,914 A | 8/1990 | Allen |
| 4,967,749 A | 11/1990 | Cohen |
| 4,986,270 A | 1/1991 | Cohen |
| 4,991,579 A | 2/1991 | Allen |
| 4,995,068 A | 2/1991 | Chou et al. |
| 4,995,398 A | 2/1991 | Turnidge |
| 5,003,976 A | 4/1991 | Alt |
| 5,024,224 A | 6/1991 | Engebretson |
| 5,025,795 A | 6/1991 | Kunig |
| 5,029,582 A | 7/1991 | Lekholm |
| 5,040,536 A | 8/1991 | Riff |
| 5,040,538 A | 8/1991 | Mortazavi |
| 5,113,859 A | 5/1992 | Funke |
| 5,139,020 A | 8/1992 | Koestner et al. |
| 5,154,171 A | 10/1992 | Chirife |
| 5,161,536 A | 11/1992 | Vilkomerson et al. |
| 5,163,429 A | 11/1992 | Cohen |
| 5,178,151 A | 1/1993 | Sackner |
| 5,178,153 A | 1/1993 | Einzig |
| 5,183,051 A | 2/1993 | Kraidin et al. |
| 5,188,106 A | 2/1993 | Nappholz et al. |
| 5,190,035 A | 3/1993 | Salo et al. |
| 5,199,428 A | 4/1993 | Obel et al. |
| 5,200,891 A | 4/1993 | Kehr et al. |
| 5,213,098 A | 5/1993 | Bennett et al. |
| 5,246,008 A | 9/1993 | Mueller |
| 5,265,615 A | 11/1993 | Frank et al. |
| 5,267,174 A | 11/1993 | Kaufman et al. |
| 5,277,191 A | 1/1994 | Hughes |
| 5,279,309 A | 1/1994 | Taylor et al. |
| 5,279,607 A | 1/1994 | Schentag et al. |
| 5,289,821 A | 3/1994 | Swartz |
| 5,300,092 A | 4/1994 | Schaldach |
| 5,314,457 A | 5/1994 | Jeutter et al. |
| 5,329,459 A | 7/1994 | Kaufman et al. |
| 5,330,505 A | 7/1994 | Cohen |
| 5,339,051 A | 8/1994 | Koehler et al. |
| 5,368,040 A | 11/1994 | Carney |
| 5,375,603 A | 12/1994 | Feiler |
| 5,394,457 A | 2/1995 | Leibinger et al. |
| 5,397,329 A | 3/1995 | Allen |
| 5,400,793 A | 3/1995 | Wesseling |
| 5,411,535 A | 5/1995 | Fujii et al. |
| 5,411,551 A | 5/1995 | Winston et al. |
| 5,417,717 A | 5/1995 | Salo et al. |
| 5,423,323 A | 6/1995 | Orth |
| 5,423,334 A | 6/1995 | Jordan |
| 5,438,990 A | 8/1995 | Wahlstrand et al. |
| 5,445,608 A | 8/1995 | Chen et al. |
| 5,454,838 A | 10/1995 | Vallana et al. |
| 5,469,859 A | 11/1995 | Tsoglin et al. |
| 5,476,488 A | 12/1995 | Morgan et al. |
| 5,488,954 A | 2/1996 | Sleva et al. |
| 5,490,962 A | 2/1996 | Cima et al. |
| 5,509,424 A | 4/1996 | Al Ali |
| 5,528,067 A | 6/1996 | Farb |
| 5,535,752 A | 7/1996 | Halperin et al. |
| 5,558,091 A | 9/1996 | Acker et al. |
| 5,562,714 A | 10/1996 | Grevious |
| 5,564,434 A | 10/1996 | Halperin et al. |
| 5,571,152 A | 11/1996 | Chen et al. |
| 5,604,531 A | 2/1997 | Iddan et al. |
| 5,605,154 A | 2/1997 | Ries et al. |
| 5,619,997 A | 4/1997 | Kaplan |
| 5,626,630 A | 5/1997 | Markowitz et al. |
| 5,628,782 A | 5/1997 | Myers et al. |
| 5,642,731 A | 7/1997 | Kehr |
| 5,643,327 A | 7/1997 | Dawson et al. |
| 5,647,369 A | 7/1997 | Petrucelli et al. |
| 5,656,428 A | 8/1997 | McAllister et al. |
| 5,704,352 A | 1/1998 | Tremblay et al. |
| 5,705,753 A | 1/1998 | Hastings et al. |
| 5,728,281 A | 3/1998 | Holmstrom et al. |
| 5,729,129 A | 3/1998 | Acker |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,752,235 A | 5/1998 | Kehr et al. |
| 5,752,976 A | 5/1998 | Duffin et al. |
| 5,755,766 A | 5/1998 | Chastain et al. |
| 5,769,877 A | 6/1998 | Barreras, Sr. |
| 5,776,324 A | 7/1998 | Usala |
| 5,792,195 A | 8/1998 | Carlson et al. |
| 5,796,827 A | 8/1998 | Coppersmith et al. |
| 5,797,395 A | 8/1998 | Martin |
| 5,800,478 A | 9/1998 | Chen et al. |
| 5,807,258 A | 9/1998 | Cimochowski et al. |
| 5,807,395 A | 9/1998 | Mulier et al. |
| 5,807,397 A | 9/1998 | Barreras |
| 5,810,009 A | 9/1998 | Mine et al. |
| 5,810,735 A | 9/1998 | Halperin et al. |
| 5,832,924 A | 11/1998 | Archibald et al. |
| 5,833,603 A | 11/1998 | Kovacs et al. |
| 5,835,455 A | 11/1998 | Hanson et al. |
| 5,836,300 A | 11/1998 | Mault |
| 5,843,135 A | 12/1998 | Weijand et al. |
| 5,855,609 A | 1/1999 | Knapp |
| 5,856,722 A | 1/1999 | Haronian et al. |
| 5,868,673 A | 2/1999 | Vesely |
| 5,873,835 A | 2/1999 | Hastings et al. |
| 5,886,267 A | 3/1999 | Ortiz |
| 5,891,180 A | 4/1999 | Greeninger et al. |
| 5,904,708 A | 5/1999 | Goedeke et al. |
| 5,911,685 A | 6/1999 | Siess et al. |
| 5,919,221 A | 7/1999 | Miesel |
| 5,941,249 A | 8/1999 | Maynard |
| 5,954,641 A | 9/1999 | Kehr et al. |
| 5,957,950 A | 9/1999 | Mockros et al. |
| 5,967,986 A | 10/1999 | Cimochowski et al. |
| 5,979,898 A | 11/1999 | Pan |
| 6,002,963 A | 12/1999 | Mouchawar et al. |
| 6,023,641 A | 2/2000 | Thompson |
| 6,024,704 A | 2/2000 | Meador et al. |
| 6,050,951 A | 4/2000 | Friedman et al. |

(56) References Cited

U.S. PATENT DOCUMENTS

| | | | |
|---|---|---|---|
| 6,053,873 A | 4/2000 | Govari et al. |
| 6,083,248 A | 7/2000 | Thompson |
| 6,112,116 A | 8/2000 | Fischell et al. |
| 6,123,861 A | 9/2000 | Santini, Jr. et al. |
| 6,140,740 A | 10/2000 | Porat et al. |
| 6,141,588 A | 10/2000 | Cox et al. |
| 6,152,885 A | 11/2000 | Taepke |
| 6,155,267 A | 12/2000 | Nelson |
| 6,161,032 A | 12/2000 | Acker |
| 6,162,238 A | 12/2000 | Kaplan et al. |
| 6,171,252 B1 | 1/2001 | Roberts |
| 6,179,767 B1 | 1/2001 | Ziegler et al. |
| 6,185,452 B1 | 2/2001 | Schulman et al. |
| 6,198,965 B1 | 3/2001 | Penner et al. |
| 6,200,265 B1 | 3/2001 | Walsh et al. |
| 6,234,973 B1 | 5/2001 | Meador et al. |
| 6,236,889 B1 | 5/2001 | Soykan et al. |
| 6,237,398 B1 | 5/2001 | Porat et al. |
| 6,239,724 B1 | 5/2001 | Doron et al. |
| 6,248,080 B1 | 6/2001 | Miesel et al. |
| 6,256,538 B1 | 7/2001 | Ekwall |
| 6,266,567 B1 | 7/2001 | Ishikawa et al. |
| 6,273,904 B1 | 8/2001 | Chen et al. |
| 6,277,078 B1 | 8/2001 | Porat et al. |
| 6,278,894 B1 | 8/2001 | Salo et al. |
| 6,298,267 B1 * | 10/2001 | Rosborough et al. ............. 607/6 |
| 6,305,381 B1 | 10/2001 | Weijand et al. |
| 6,308,099 B1 | 10/2001 | Fox et al. |
| 6,314,323 B1 | 11/2001 | Ekwall |
| 6,330,957 B1 | 12/2001 | Bell-Greenstreet |
| 6,331,163 B1 | 12/2001 | Kaplan |
| 6,368,275 B1 | 4/2002 | Sliwa et al. |
| 6,394,958 B1 | 5/2002 | Bratteli et al. |
| 6,397,661 B1 | 6/2002 | Grimes et al. |
| 6,409,674 B1 | 6/2002 | Brockway et al. |
| 6,409,675 B1 | 6/2002 | Turcott |
| 6,411,850 B1 | 6/2002 | Kay et al. |
| 6,416,474 B1 | 7/2002 | Penner et al. |
| 6,421,565 B1 | 7/2002 | Hemmingsson |
| 6,431,175 B1 | 8/2002 | Penner et al. |
| 6,432,050 B1 | 8/2002 | Porat et al. |
| 6,438,408 B1 | 8/2002 | Mulligan et al. |
| 6,441,747 B1 | 8/2002 | Khair et al. |
| 6,442,413 B1 | 8/2002 | Silver |
| 6,445,953 B1 | 9/2002 | Bulkes et al. |
| 6,456,883 B1 | 9/2002 | Torgerson et al. |
| 6,471,645 B1 | 10/2002 | Warkentin et al. |
| 6,472,991 B1 | 10/2002 | Schulman et al. |
| 6,475,147 B1 | 11/2002 | Yost et al. |
| 6,475,170 B1 | 11/2002 | Doron et al. |
| 6,486,588 B2 | 11/2002 | Doron et al. |
| 6,504,286 B1 | 1/2003 | Porat et al. |
| 6,522,914 B1 | 2/2003 | Huvelle et al. |
| 6,567,700 B1 | 5/2003 | Turcott et al. |
| 6,574,510 B2 | 6/2003 | Von Arx et al. |
| 6,580,946 B2 | 6/2003 | Struble |
| 6,604,000 B2 | 8/2003 | Lu |
| 6,607,485 B2 | 8/2003 | Bardy |
| 6,609,023 B1 | 8/2003 | Fischell et al. |
| 6,615,083 B2 * | 9/2003 | Kupper ............................ 607/25 |
| 6,622,049 B2 | 9/2003 | Penner et al. |
| 6,628,989 B1 | 9/2003 | Penner et al. |
| 6,638,231 B2 | 10/2003 | Govari et al. |
| 6,644,322 B2 | 11/2003 | Webb |
| 6,654,638 B1 | 11/2003 | Sweeney |
| 6,675,049 B2 | 1/2004 | Thompson et al. |
| 6,699,186 B1 | 3/2004 | Wolinsky et al. |
| 6,702,847 B2 | 3/2004 | DiCarlo |
| 6,708,061 B2 | 3/2004 | Salo et al. |
| 6,708,065 B2 | 3/2004 | Von Arx et al. |
| 6,712,772 B2 | 3/2004 | Cohen et al. |
| 6,720,709 B2 | 4/2004 | Porat et al. |
| 6,720,887 B1 | 4/2004 | Zunti |
| 6,733,447 B2 | 5/2004 | Lai et al. |
| 6,738,667 B2 | 5/2004 | Deno et al. |
| 6,738,671 B2 | 5/2004 | Christophersom et al. |
| 6,743,173 B2 | 6/2004 | Penner et al. |
| 6,758,822 B2 | 7/2004 | Romano |
| 6,764,446 B2 | 7/2004 | Wolinsky et al. |
| 6,782,810 B2 | 8/2004 | Vilo |
| 6,783,499 B2 | 8/2004 | Schwartz |
| 6,792,308 B2 | 9/2004 | Corbucci |
| 6,792,311 B2 | 9/2004 | Fox et al. |
| 6,805,667 B2 | 10/2004 | Christopherson et al. |
| 6,809,507 B2 | 10/2004 | Morgan et al. |
| 6,824,512 B2 | 11/2004 | Warkentin et al. |
| 6,832,112 B1 | 12/2004 | Bornzin |
| 6,840,956 B1 | 1/2005 | Wolinsky et al. |
| 6,855,115 B2 | 2/2005 | Fonseca et al. |
| 6,859,665 B2 | 2/2005 | Ding et al. |
| 6,865,419 B2 | 3/2005 | Mulligan et al. |
| 6,868,346 B2 | 3/2005 | Larson et al. |
| 6,869,404 B2 | 3/2005 | Schulhauser et al. |
| 6,871,088 B2 | 3/2005 | Chinchoy |
| 6,885,889 B2 | 4/2005 | Chinchoy |
| 6,889,086 B2 | 5/2005 | Mass et al. |
| 6,895,265 B2 | 5/2005 | Silver |
| 6,907,285 B2 | 6/2005 | Denker et al. |
| 6,915,162 B2 | 7/2005 | Noren et al. |
| 6,926,670 B2 | 8/2005 | Rich et al. |
| 6,937,900 B1 | 8/2005 | Pianca et al. |
| 6,949,075 B2 | 9/2005 | Hatlesad et al. |
| 6,961,448 B2 | 11/2005 | Nichols et al. |
| 6,970,742 B2 | 11/2005 | Mann et al. |
| 6,978,182 B2 | 12/2005 | Mazar et al. |
| 6,985,773 B2 | 1/2006 | Von Arx et al. |
| 6,993,393 B2 | 1/2006 | Von Arx et al. |
| 7,003,350 B2 | 2/2006 | Denker et al. |
| 7,018,336 B2 | 3/2006 | Enegren et al. |
| 7,024,248 B2 | 4/2006 | Penner et al. |
| 7,033,322 B2 | 4/2006 | Silver |
| 7,035,684 B2 | 4/2006 | Lee |
| 7,047,065 B2 | 5/2006 | Kalgren et al. |
| 7,048,691 B2 | 5/2006 | Miele et al. |
| 7,060,030 B2 | 6/2006 | Von Arx et al. |
| 7,061,381 B2 | 6/2006 | Forcier et al. |
| 7,088,254 B2 | 8/2006 | Liebenow |
| 7,090,648 B2 | 8/2006 | Sackner et al. |
| 7,127,290 B2 | 10/2006 | Girouard et al. |
| 7,130,681 B2 * | 10/2006 | Gebhardt et al. .................. 607/6 |
| 7,134,999 B2 | 11/2006 | Brauker et al. |
| 7,136,703 B1 | 11/2006 | Cappa et al. |
| 7,160,252 B2 | 1/2007 | Cho et al. |
| 7,181,268 B2 | 2/2007 | Sheldon et al. |
| 7,195,594 B2 | 3/2007 | Eigler et al. |
| 7,198,603 B2 | 4/2007 | Penner et al. |
| 7,200,439 B2 | 4/2007 | Zdeblick et al. |
| 7,203,545 B2 | 4/2007 | Schmitt et al. |
| 7,204,798 B2 | 4/2007 | Zdeblick et al. |
| 7,209,790 B2 | 4/2007 | Thompson et al. |
| 7,212,861 B1 | 5/2007 | Park et al |
| 7,214,189 B2 | 5/2007 | Zdeblick |
| 7,236,821 B2 | 6/2007 | Cates et al. |
| 7,248,923 B2 | 7/2007 | Maile et al. |
| 7,273,457 B2 | 9/2007 | Penner |
| 7,294,105 B1 | 11/2007 | Islam |
| 7,335,161 B2 * | 2/2008 | Von Arx et al. ............... 600/485 |
| 7,399,313 B2 | 7/2008 | Brown et al. |
| 7,425,200 B2 | 9/2008 | Brockway et al. |
| 7,452,334 B2 | 11/2008 | Gianchandani et al. |
| 7,481,771 B2 | 1/2009 | Fonseca et al. |
| 7,742,815 B2 | 6/2010 | Sale et al. |
| 2001/0051766 A1 | 12/2001 | Gazdzinski |
| 2001/0051787 A1 | 12/2001 | Haller et al. |
| 2002/0022785 A1 | 2/2002 | Romano |
| 2002/0023123 A1 | 2/2002 | Madison |
| 2002/0042561 A1 | 4/2002 | Schulman et al. |
| 2002/0045812 A1 | 4/2002 | Ben-Haim et al. |
| 2002/0045836 A1 | 4/2002 | Alkawwas |
| 2002/0062086 A1 | 5/2002 | Miele et al. |
| 2002/0103454 A1 | 8/2002 | Sackner et al. |
| 2002/0120204 A1 | 8/2002 | Pfeiffer et al. |
| 2002/0126036 A1 | 9/2002 | Flaherty et al. |
| 2002/0147406 A1 | 10/2002 | von Segesser |

(56) References Cited

U.S. PATENT DOCUMENTS

| | | |
|---|---|---|
| 2002/0151770 A1 | 10/2002 | Noll, III et al. |
| 2002/0183628 A1 | 12/2002 | Reich et al. |
| 2002/0188323 A1 | 12/2002 | Penner et al. |
| 2003/0009204 A1 | 1/2003 | Amundson et al. |
| 2003/0023173 A1 | 1/2003 | Bratteli et al. |
| 2003/0045805 A1 | 3/2003 | Sheldon et al. |
| 2003/0060723 A1* | 3/2003 | Joo et al. ............. 600/510 |
| 2003/0114897 A1 | 6/2003 | Von Arx et al. |
| 2003/0136417 A1 | 7/2003 | Fonseca et al. |
| 2003/0181794 A1 | 9/2003 | Rini et al. |
| 2003/0191383 A1 | 10/2003 | Ben-Haim et al. |
| 2003/0199779 A1 | 10/2003 | Muhlenberg |
| 2004/0032187 A1 | 2/2004 | Penner et al. |
| 2004/0044393 A1 | 3/2004 | Yarden et al. |
| 2004/0064133 A1 | 4/2004 | Miller et al. |
| 2004/0077937 A1 | 4/2004 | Yarden |
| 2004/0122484 A1 | 6/2004 | Hatlestad et al. |
| 2004/0122486 A1 | 6/2004 | Stahmann et al. |
| 2004/0152999 A1 | 8/2004 | Cohen et al. |
| 2004/0158163 A1 | 8/2004 | Cohen et al. |
| 2004/0167416 A1 | 8/2004 | Lee |
| 2004/0172081 A1 | 9/2004 | Wang |
| 2005/0056539 A1 | 3/2005 | Morgan et al. |
| 2005/0102002 A1 | 5/2005 | Salo et al. |
| 2005/0109338 A1 | 5/2005 | Stahmann et al. |
| 2005/0109339 A1 | 5/2005 | Stahmann et al. |
| 2005/0124904 A1 | 6/2005 | Roteliuk |
| 2005/0137490 A1 | 6/2005 | Scheiner et al. |
| 2005/0149143 A1 | 7/2005 | Libbus et al. |
| 2005/0154321 A1 | 7/2005 | Wolinsky et al. |
| 2005/0159639 A1 | 7/2005 | Skliar et al. |
| 2005/0159789 A1 | 7/2005 | Brockway et al. |
| 2005/0182330 A1 | 8/2005 | Brockway et al. |
| 2005/0187482 A1 | 8/2005 | O'Brien et al. |
| 2005/0192637 A1 | 9/2005 | Girouard et al. |
| 2005/0192844 A1 | 9/2005 | Esler et al. |
| 2005/0197585 A1 | 9/2005 | Brockway et al. |
| 2005/0215887 A1 | 9/2005 | Ben-Haim et al. |
| 2005/0242479 A1 | 11/2005 | Petisce et al. |
| 2005/0256544 A1 | 11/2005 | Thompson |
| 2005/0265999 A1 | 12/2005 | Bush et al. |
| 2005/0267379 A1 | 12/2005 | Pfeiffer et al. |
| 2005/0288727 A1 | 12/2005 | Penner |
| 2006/0009818 A1 | 1/2006 | Von Arx et al. |
| 2006/0031378 A1 | 2/2006 | Vallapureddy et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0089694 A1 | 4/2006 | Zhang et al. |
| 2006/0122522 A1 | 6/2006 | Chavan et al. |
| 2006/0136004 A1 | 6/2006 | Cowan et al. |
| 2006/0142651 A1 | 6/2006 | Brister et al. |
| 2006/0167359 A1 | 7/2006 | Bennett et al. |
| 2006/0167361 A1 | 7/2006 | Bennett et al. |
| 2006/0235323 A1 | 10/2006 | Hatib et al. |
| 2007/0043394 A1 | 2/2007 | Zhang et al. |
| 2007/0049977 A1 | 3/2007 | Von Arx et al. |
| 2007/0060959 A1* | 3/2007 | Salo et al. ............. 607/6 |
| 2007/0088221 A1 | 4/2007 | Stahmann |
| 2007/0129765 A1 | 6/2007 | Gilkerson et al. |
| 2007/0142727 A1 | 6/2007 | Zhang et al. |
| 2007/0142866 A1 | 6/2007 | Li et al. |
| 2007/0149890 A1 | 6/2007 | Li et al. |
| 2007/0161914 A1 | 7/2007 | Zdeblick et al. |
| 2007/0197921 A1 | 8/2007 | Cohen et al. |
| 2007/0282210 A1 | 12/2007 | Stern |
| 2007/0282381 A1 | 12/2007 | Li et al. |
| 2008/0015421 A1 | 1/2008 | Penner |
| 2008/0015651 A1* | 1/2008 | Ettori et al. ............. 607/17 |
| 2008/0021333 A1 | 1/2008 | Huelskamp |
| 2008/0021972 A1 | 1/2008 | Huelskamp et al. |
| 2008/0046037 A1 | 2/2008 | Haubrich et al. |
| 2008/0051843 A1 | 2/2008 | Li et al. |
| 2008/0071178 A1 | 3/2008 | Greenland et al. |
| 2008/0077440 A1 | 3/2008 | Doron |
| 2008/0243007 A1 | 10/2008 | Liao et al. |
| 2009/0201148 A1 | 8/2009 | Tran et al. |
| 2009/0228078 A1 | 9/2009 | Zhang et al. |
| 2010/0056931 A1 | 3/2010 | Soffer et al. |
| 2010/0094144 A1 | 4/2010 | Doron |
| 2010/0125211 A1 | 5/2010 | Stahmann et al. |
| 2010/0222833 A1 | 9/2010 | Salo et al. |
| 2010/0324378 A1 | 12/2010 | Tran et al. |

FOREIGN PATENT DOCUMENTS

| | | |
|---|---|---|
| EP | 1266606 | 12/2002 |
| EP | 1169085 | 8/2004 |
| JP | 03-034196 | 2/1991 |
| JP | 10-055202 | 2/1998 |
| JP | 2004-528152 | 9/2004 |
| JP | 2005-253657 | 9/2005 |
| JP | 2006-523120 | 10/2006 |
| JP | 2007-516796 | 6/2007 |
| JP | 2007-519441 | 7/2007 |
| WO | WO83/03345 | 10/1983 |
| WO | WO95/03086 | 2/1995 |
| WO | WO95/27531 | 10/1995 |
| WO | WO97/01986 | 1/1997 |
| WO | WO 97/18856 | 5/1997 |
| WO | WO97/32519 | 9/1997 |
| WO | WO97/33513 | 9/1997 |
| WO | WO97/47236 | 12/1997 |
| WO | WO98/26716 | 6/1998 |
| WO | WO98/29030 | 7/1998 |
| WO | WO99/17095 | 4/1999 |
| WO | WO99/26530 | 6/1999 |
| WO | WO99/34453 | 7/1999 |
| WO | WO99/47205 | 9/1999 |
| WO | WO99/55223 | 11/1999 |
| WO | WO99/55225 | 11/1999 |
| WO | WO99/59460 | 11/1999 |
| WO | WO99/66988 | 12/1999 |
| WO | WO00/16686 | 3/2000 |
| WO | WO00/58744 | 10/2000 |
| WO | WO01/28627 | 4/2001 |
| WO | WO01/56467 | 8/2001 |
| WO | WO01/74278 | 10/2001 |
| WO | WO 01/76687 | 10/2001 |
| WO | WO 01/85094 | 11/2001 |
| WO | WO02/03347 | 1/2002 |
| WO | WO02/32502 | 4/2002 |
| WO | WO03/002243 | 1/2003 |
| WO | WO03/096889 | 11/2003 |
| WO | WO 2004/012808 | 2/2004 |
| WO | WO 2004/091719 | 10/2004 |
| WO | WO 2005/000206 | 1/2005 |
| WO | WO 2005/063332 | 7/2005 |
| WO | WO 2005/065771 | 7/2005 |
| WO | WO2005/089638 | 9/2005 |
| WO | WO2005/118056 | 12/2005 |
| WO | WO2006/033812 | 3/2006 |
| WO | WO2006/034183 | 3/2006 |
| WO | WO2006/045073 | 4/2006 |
| WO | WO2006/045074 | 4/2006 |
| WO | WO2006/045075 | 4/2006 |
| WO | WO2006/069215 | 6/2006 |
| WO | WO 2006/124833 | 11/2006 |
| WO | WO2007/030474 | 3/2007 |
| WO | WO2007/047287 | 4/2007 |
| WO | WO2007/070794 | 6/2007 |
| WO | WO2007/099533 | 9/2007 |
| WO | WO2008/011570 | 1/2008 |

(56) References Cited

FOREIGN PATENT DOCUMENTS

| WO | WO2008/011592 | 1/2008 |
|---|---|---|
| WO | WO2008/011593 | 1/2008 |
| WO | WO2008/154145 | 12/2008 |

OTHER PUBLICATIONS

Takazawa et al., "Assessment of Vasoactive Agents and Vascular Aging by the Second Derivative of Photoplethysmogram Waveform", Hypertension, 1998, 32:365-370.

Fink, Mathias, "Time Reversal of Ultrasonic Fields—Part I: Basic Principles", IEEE Transactions on Ultrasonics, Ferroelectrics, and Frequency Control, vol. 39, No. 5, Sep. 1992, pp. 555-566.

Wu, Francois et al., "Time Reversal of Ultrasonic Fields—Part II: Experimental Results", IEEE Transactions on Ultrasonics, Ferroelectrics, and Frequency Control, vol. 39, No. 5, Sep. 1992, pp. 567-578.

Strickberger, S. Adam et al., "Extracardiac Ablation of the Canine Atrioventricular Junction by Use of High-Intensity Focused Ultrasound", Circulation, Jul. 13, 1999; downloaded from circ.ahajournals.org at ACS/GUIDANT on Jan. 4, 2008, pp. 203-208.

Bourgeois, Maurice J. et al., "Continuous Determination of Beat-to-Beat Stroke Volume from Aortic pressure Pulses in the Dog", Circulation Research, vol. 39, pp. 15-24 (1976).

Rozenman, Yoseph et al., "Wireless Acoustic Communication With a Miniature Pressure Sensor in the Pulmonary Artery for Disease Surveillance and Therapy of Patients With Congestive Heart Failure", Journal of the American College of Cardiology, 49:7, 2007, pp. 784-789.

Wesseling, KH et al., "Computation of Aortic Flow From Pressure in Humans Using a Nonlinear, Three-Element Model", Journal of Applied Physiology, vol. 74, Issue 5, pp. 2566-2573 (1993).

International Search Report and Written Opinion issued in PCT/US2009/033211, mailed Sep. 21, 2009, 14 pages.

Cohen, T.J. et al., "A Hemodynamically Responsive Antitachycardia System. Development and Basis for Design in Humans", Circulation 1990, vol. 82, No. 2, pp. 394-406, XP002560584.

Blacher, Jacques et al., "Aortic Pulse Wave Velocity as a Member of Cardiovascular Risk in Hypertensive Patients", Hypertension May 1999;33;1111-1117.

Farzaneh-Far, Ramin et al., Usefulness of Noninvasive Estimate of Pulmonary Vascular Resistance to predict Mortality, Heart Failure, and Adverse Cardiovascular Events in Patients With Stable Coronary Artery Disease (from the Heart and Soul Study), The American Journal of Cardiology, vol. 101, Issue 6, Mar. 15, 2008, pp. 762-766.

El Gamal, M.I.H. et al., "Chronic Ventricular Pacing With Ventriculo-Atrial Conduction Versus Atrial Pacing in Three Patients With Symptomatic Sinus Bradycardia", PACE, vol. 4, Jan.-Feb. 1981, pp. 100-106.

Fujiki, Akira et al., "Pacemaker Syndrome Evaluated by Cardiopulmonary Exercise Testing", PACE, vol. 13, Oct. 1990, pp. 1236-1241.

B. C. Penney et al., "Simplified electrode array for impedance cardiography," Medical & Biological Engineering & Computing, 1985, 23, p. 1-7.

B. Henderson et al., "Interaction of Photodynamic Therapy and Hyperthermia: Tumor Response and Cell Survival after Treatment of Mice in Vivo," Cancer Research, vol. 45, 6071 (Dec. 1985).

Bennett et al., "Subcutaneous pressure measurement as a surrogate for an external pressure reference for chronic implantable pressure monitoring," Journal of Cardial Failure, Churchill Livingstone, vol. 9, No. 5, p. S51, Oct. 1, 2003, abstract only.

Bonnefoy E, Ninet J, Robin J, Leroux F, Boissonat P, Brule P, Champsaur G., 1994, Bipolar intramyocardial electrogram from an implanted telemetric pacemaker for the diagnosis of cardiac allograft rejection, Pacing Clin Electrophysiol, 17(11 Pt 2):2052-6.

C. Hierold et al. (Germany, 1998) "Implantable Low Power Integrated Pressure Sensor System for Minimal Invasive Telemetric Patient Monitoring" IEEE, pp. 568-573.

Dipl.-Ing. Torsten Eggers et al. (Germany) "Implantable Telemetric Endosytem (ITES)" IMSAS Institut Fur Mikrosensoren-Aktuatoren Und-Systeme, 1998. 2 pp.

E R. Cosman et al. (Massachussetts, Apr. 1979) "A Telemetric Pressure Sensor for Ventricular Shunt Systems" Surgical Neurology vol. 11, No. 4, pp. 287-294.

G.W.H. Schurink et al. (1998) "Late Endoleak After Endovascular Therapy for Abdominal Aortic Aneurysm" Eur. J. Vasc. Endovasc. Surg. vol. 17, pp. 448-450.

Gerhausser A, Reichel T, Neukomm P A, Bolz A, Hugel J, Schaldach M, 1997, Diagnosis of rejection after kidney transplantation by impedance spectroscopy with an implantable measuring system, Biomed Tech (Berl), 42 Suppl. 160-1.

GH White et al. (1997) "Endoleak Following Endoluminal Repair of AAA: Management Options and Patient Outcomes", J. Endovasc Surg, pp. 1-45.

Graichen et al., "Patient Monitoring System for Load Measurement with Spinal Fixation Devices," Med. Eng. Phys. 18, (1996), pp. 167-174.

Haas et al., "Photodynamic Effects of Dyes on Bacteria," Published in Mutation Research, 1979, vol. 60, pp. 1-11.

Hashima et al., "Nonhomogenous Analysis of Epicardial Strain Distributions During Acute Myocardial Ischemia in the Dog," J Biomech Jan. 26, 1993: 19-35.

Hetzer R. et al., 1998, Daily non-invasive rejection monitoring improves long-term survival in pediatric heart transplantation, Ann. Thorac. Surg. (66):1343-1349.

J.A. Parrish, "Photobiologic Consideration on Photoradiation Therapy," pp. 91-108, Porphyrin Photosensitization, Plenum Press, (1983).

K.E. Uhrich et al., "Synthesis and characterization of degradable poly(anhydride-co-imides)", Macromolecules, 1995, 28, 2184-93.

Karl E. Richard et al. (Germany, Jan. 1999) "First clinical results with a telemetric shunt-integrated ICP-sensor" Neurological Research vol. 21, pp. 117-120.

Labrousse and Satre, "Photodynamic Killing of *Dictyostelium discoideum* Amoebae Mediated by 4',5'-Diiodoflurescin Isothiocyanate Dextran. A strategy for the isolation of Thermoconditional Endocytosis Mutants," published in Photochemistry and Photobiology, 1993, vol. 67, No. 3, pp. 531-537.

Mackay et al., "Bio-medical Telemetry: Sensing and Transmitting Biological Information from Animals and Man," John Wiley & Sons, Inc. New York (1970) pp. 244-245.

Pfitzmann R, Muller J, Grauhan O. Cohnert T, Hetzer R, Z Kardiol, 1998, Measuring bioelectric myocardial impedance as a non invasive method for diagnosis of graft rejection after heart transplantation, 87(4):258-266.

Pirolo J S, Shuman T S, Brunt E M, Liptay M J, Cox J L, Ferguson T B Jr., J Thoracic Cardiovasc Surg, 1992, Noninvasive detection of cardiac allograft rejection by prospective telemetric monitoring, 103(5):969-79.

Prof. Dr. Johannes Zacheja et al. (Germany, Sep. 1996) "An Implantable Microsystem for Biomedical Applications" Micro System Technologies 96, pp. 717-722.

S.K. Gupta et al. (1999) "Use of a Piezoelectric Film Sensor for Monitoring Vascular Grafts", The American Journal of Surgery, vol. 160, pp. 182-186.

T. Chuter et al. (Sweden, Jan. 1997) "Aneurysm Pressure Following Endovascular Exclusion" Eur. J. Vasc. Endovasc. Surg. vol. 13, pp. 85-87.

T.A. Cochran et al. (1990) "Aortic Aneurysm Abdominal", Current Therapy in Adult Medicine, Fourth Edition.

Z. Tang et al. (May 1995) "Data Transmission from an Implantable Biotelemeter by Load-Shift Keying Using Circuit Configuration Modulator" IEEE Transactions on Biomedical Engineering. vol. 42, No. 5, pp. 524-528.

Zacharoulis, A.A. et al., "Measurement of stroke volume from pulmonary artery pressure record in man", British Heart Journal, 1975, vol. 37, pp. 20-25.

Humphrey, Chester B. et al., "An analysis of direct and indirect measurements of left atrial filling pressure", The Journal of Thoracic and Cardiovascular Surgery, vol. 71, No. 5, May 1976, pp. 643-647.

(56) References Cited

OTHER PUBLICATIONS

"Pulmonary Valve", from Wikipedia, the free encyclopedia, http://en.wikipedia.org/wiki/Pulmonary_valve.

"Cardiac Output", from Wikipedia, the free encyclopedia, http://en.wikipedia.org/wiki/Cardiac_output.

* cited by examiner

METHODS OF MONITORING HEMODYNAMIC STATUS FOR RHYTHM DISCRIMINATION WITHIN THE HEART

CROSS-REFERENCE TO RELATED APPLICATION

This application claims priority under 35 U.S.C. §119 to U.S. Provisional Application No. 61/027,683, filed on Feb. 11, 2008, entitled "Methods Of Monitoring Hemodynamic Status For Rhythm Discrimination Within The Heart," which is incorporated herein by reference in its entirety.

TECHNICAL FIELD

The present disclosure relates generally to the field of implantable medical devices. More specifically, the present disclosure pertains to systems and methods of monitoring hemodynamic status for rhythm discrimination within a patient.

BACKGROUND

Implantable medical devices (IMDs) such as pacemakers and implantable cardioverter defibrillators are utilized in monitoring and regulating various conditions within the body. An implantable cardioverter defibrillator, for example, is often utilized in cardiac rhythm management applications to monitor the rate and rhythm of the heart and for delivering various therapies such as cardiac pacing, cardiac defibrillation, and/or cardiac therapy. In some systems, the implantable cardiac defibrillator can be configured to sense various physiological parameters occurring in the atria and/or ventricles of the body to determine the occurrence of any abnormalities in the operation of the patient's heart. Based on these sensed parameters, an appropriate therapy may then be delivered to the patient.

Present techniques used for detecting events occurring within the heart are sometimes ineffective at discriminating between subtle differences in electrical heart activity, which can affect the type of treatment provided to the patient. In the detection of an event such as ventricular tachycardia (VT), for example, many present techniques are unable to accurately differentiate the event from another event such as a wide-complex supraventricular tachycardia (SVT), which often appears similar to ventricular tachycardia on an electrocardiogram (ECG) or electrogram (EGM). In contrast to ventricular tachycardia, the occurrence of supraventricular tachycardia may not be problematic, and may entail a different, less drastic form of therapy. Ventricular tachycardia, on the other hand, is a potentially lethal condition, and requires immediate medical therapy often in the form of shock therapy.

To discriminate between these events, many IMDs utilize interval-based and/or morphology-based algorithms, which rely on the analysis of electrical signals from an ECG or EGM. In some cases, the presence of electrical noise or interference within the body due to the pacing artifact (e.g., noise generated by a pacemaker) or from other sources may affect the ability of the sensor leads to accurately detect signals. While such techniques are effective in detecting certain types of events, they are sometimes ineffectual in discriminating between events such as ventricular tachycardia and supraventricular tachycardia.

SUMMARY

The present disclosure relates to systems and methods of performing rhythm discrimination within the body based on sensed hemodynamic signals. In some embodiments, the method includes the steps of receiving an electrical activity signal from an electrode located within or adjacent to the heart, detecting an event of the heart based on the received electrical activity signal, sensing one or more mechanical measurements using a sensor located within the body, analyzing a mechanical activity signal received from the sensor, and confirming the event detected based on an analysis of the mechanical and electrical activity signals. In some embodiments, the sensor comprises a single pressure sensor implanted at a location within the body such as the main pulmonary artery, and is configured to sense both atrial contractions and ventricular contractions of the heart. Based on the type of event confirmed by analyzing the mechanical and electrical signals, an appropriate type of therapy may then be provided to the patient.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
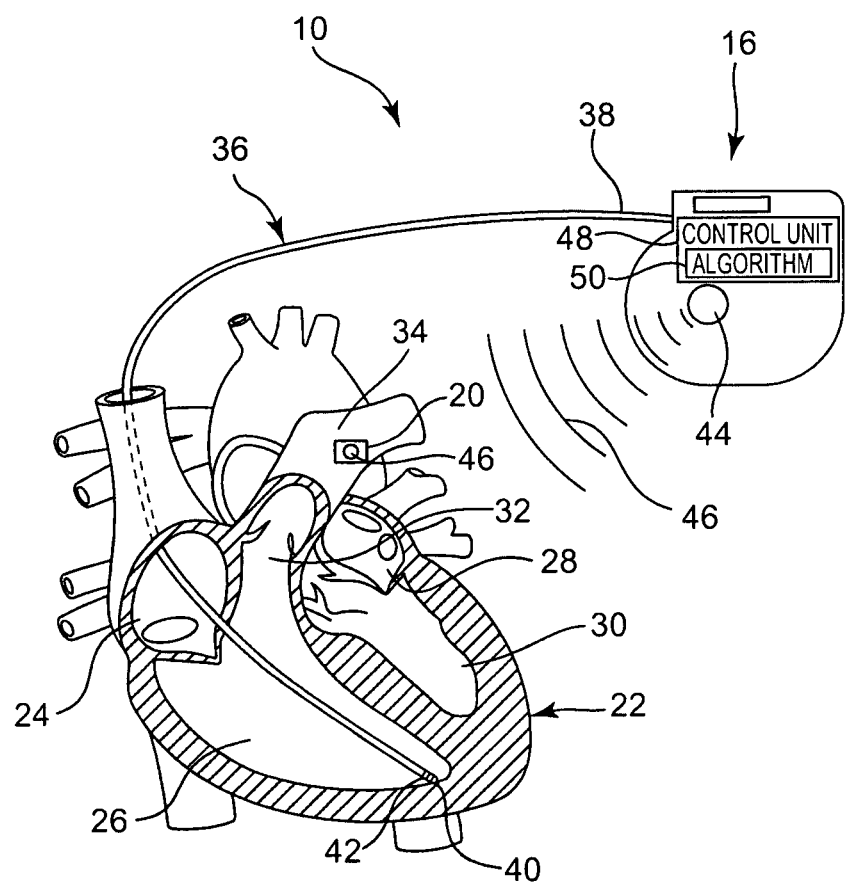
FIG. 1 is a schematic view of an illustrative system for providing cardiac rhythm management to a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an illustrative system 10 for providing cardiac rhythm management to a patient. In the embodiment of FIG. 1, the system 10 includes a pulse generator 16 implanted within the body at a location below the patient's skin, and a remote sensor 20 implanted deeply within the patient's body such as in one of the arteries or ventricles of the patient's heart 22 or in one of the pulmonary arteries such as the main pulmonary artery 34, as shown. The heart 22 includes a right atrium 24, a right ventricle 26, a left atrium 28, and a left ventricle 30. The right ventricle 26 includes an outflow tract 32, which leads to the main pulmonary artery 34.

The pulse generator 16 can be implanted subcutaneously within the body, typically at a location such as in the patient's chest or abdomen, although other implantation locations are possible. In the illustrative CRM system 10 depicted, the pulse generator 16 is coupled to a lead 36 deployed in the patient's heart 22. A proximal portion 38 of the lead 36 can be coupled to or formed integrally with the pulse generator 16. A distal portion 40 of the lead 36, in turn, can be implanted at a desired location in or near the heart 22 such as the right ventricle 26, as shown. In use, an exposed electrode 42 on the distal portion 40 of the lead 36 may provide therapy to the patient in the form of an electrical current to the heart 22.

Although the illustrative system 10 depicts only a single lead 36 inserted into the patient's heart 22, the system 10 may include multiple leads so as to electrically stimulate other areas of the heart 22. In some embodiments, for example, the distal portion of a second lead (not shown) may be implanted in the right atrium 24 for providing electrical stimulation to the atrium 24. In addition, or in lieu, another lead may be implanted in or near the left side of the heart 22 (e.g., in the coronary veins) to stimulate the left side of the heart 22. Other types of leads such as epicardial leads may also be utilized in addition to, or in lieu of, the lead 36 depicted in FIG. 1.

During operation, the lead 36 can be configured to convey electrical signals between the pulse generator 16 and the heart 22. In those embodiments where the pulse generator 16 is a pacemaker, for example, the lead 36 can be utilized to deliver electrical therapeutic stimulus for pacing the heart 22. In those embodiments where the pulse generator 16 is an implantable cardiac defibrillator, the lead 36 can be utilized to provide electric shocks to the heart 22 in response to an event such as ventricular tachycardia or bradycardia. In some embodiments, the pulse generator 16 includes both pacing and defibrillation capabilities.

The sensor 20 can be configured to perform one or more designated functions, including the sensing of one or more physiological parameters within the body. Example physiological parameters that can be measured using the sensor 20 include, but are not limited to, blood pressure, blood flow, temperature, and strain. Various electrical, chemical and/or magnetic properties may also be sensed within the body via the sensor 20. The specific configuration and function of the sensor 20 will typically vary depending on the particular therapeutic needs of the patient. In one embodiment, for example, the sensor 20 comprises a single pressure sensor implanted at a location deep within the body such as in the main pulmonary artery 34 or a branch of the main pulmonary artery 34 (e.g., in the right or left pulmonary artery). An illustrative pressure sensor suitable for use in sensing mechanical activity within the body is described, for example, in U.S. Pat. No. 6,764,446, entitled "Implantable Pressure Sensors and Methods for Making and Using Them," the contents of which is incorporated herein by reference in its entirety. In other embodiments, however, the sensor 20 can be implanted at other locations within the body, and can be configured to measure other parameters. Examples of other implantation locations can include, but are not limited to, the right atrium 24, the right ventricle 26, the left atrium 28, the left ventricle 30, or the coronary arteries. An example sensor that can be anchored within the body is described in U.S. patent application Ser. No. 11/855,725, entitled "Anchor For An Implantable Sensor," the contents of which is incorporated herein by reference in its entirety.

In the illustrative embodiment of FIG. 1, a single sensor 20 is used to simultaneously sense mechanical activity occurring within both the right atrium 24 and the right ventricle 26 of the heart 22. In some embodiments, the sensor 20 is a wireless sensor in communication with the pulse generator 16 via an acoustic, inductive, or RF telemetry link. In the illustrative system 10 depicted, for example, the pulse generator 16 includes an ultrasonic transducer 44 in acoustic communication with an ultrasonic transducer 46 coupled to the sensor 20, which together permit bidirectional wireless communications between the sensor 20 and pulse generator 16. In other embodiments, the sensor 20 is connected to the pulse generator 16 via a wired connection such as a lead.

The mechanical activity signals received from the sensor 20 can be used to confirm the existence of an electrical event detected by sense electrodes implanted within or adjacent to the heart 22, and to differentiate between types of aberrant events occurring within the heart 22. For example, in some embodiments the mechanical activity sensed by the sensor 20 can be used in conjunction with electrical activity signals received by the pulse generator 16 (e.g., from a sense electrode implanted at or near the sinus (SA) node or atrioventricular (AV) node) to differentiate between a ventricular tachycardia event versus a supraventricular tachycardia event, between a hemodynamically perfused versus non-perfused tachyarrhythmia event, or other such event.

The sensor 20 can be used in conjunction with the pulse generator 16 to optimize pacing and/or defibrillation therapy, to predict decompensation of a heart failure patient, or to provide other monitoring and/or therapy functions. In certain embodiments, for example, the sensor 20 is utilized in conjunction with an ICD to provide cardiac defibrillation to the patient as needed. Other devices such as a pulmonary sound sensor, satellite pacing device, or other such sensing and/or therapy-delivering device may also be used in conjunction with the pulse generator 16 and sensor 20.

The pulse generator 16 includes a control unit 48 which receives the electrical signals from the various leads and sensors and transmits an appropriate therapy to the patient in response. In some embodiments, the control unit 48 is configured to run a control algorithm 50 which, as discussed further herein, can be used to analyze the electrical and mechanical signals to determine the presence of an arrhythmic event such as a tachycardia or bradycardia, or for performing other rhythm discrimination within the heart.

Figure 2:
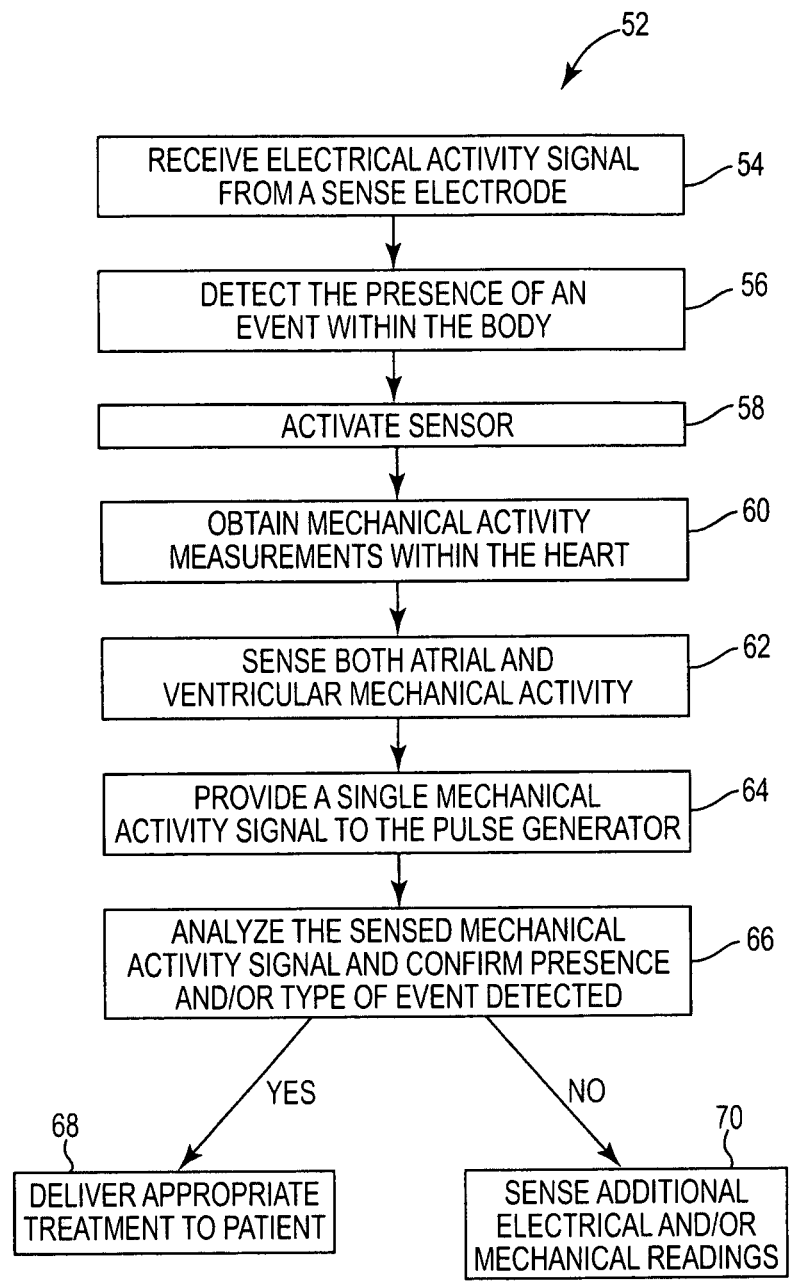
FIG. 2 is a flow chart showing an illustrative method of rhythm discrimination within the body using sensed hemodynamic signals.

FIG. 2 is a flow chart showing an illustrative method 52 of performing rhythm discrimination within a patient's body using sensed hemodynamic signals from the sensor 20 of FIG. 1. In the illustrative embodiment of FIG. 2, the method 52 begins generally at blocks 54 and 56 with the steps of receiving an electrical signal from a sense electrode implanted in or near the heart and detecting the presence of an event within the body. In certain embodiments, for example, electrical signals received from an electrode inserted at or near the sinoatrial (SA) node of the heart are analyzed by the control unit 48 to determine the presence of an event such as an arrhythmia. An example event that can be detected in some embodiments is the occurrence of a sudden acceleration of the patient's heart rate in which a majority of the heart beats are faster than a preset threshold level for a preset duration. The detection of an event may occur by analyzing electrical activity at other locations in or near the heart such as in the heart muscle of the right ventricle.

Once an event is detected (block 56), the sensor 20 may be activated (block 58) and tasked to take measurements of the mechanical activity within the heart to confirm the presence of the event and/or to ascertain more information about the particular event. Activation of the sensor 20 can occur, for example, when an event such as tachyarrhythmia is suspected based upon an analysis of the electrical signals received from the electrode or electrodes tasked to monitor electrical activity within the heart. In some embodiments, activation of the sensor 20 can occur by sending a wake-up signal to the sensor 20, causing the sensor 20 to switch between an initial, low-power state to an active, sensing state. In one embodiment, for example, the wake-up signal comprises a wake-up signal such as that described in U.S. Pat. No. 6,628,989 to Penner et al., entitled "Acoustic Switch and Apparatus and Methods For Using Acoustic Switches Within A Body," the contents of which is incorporated herein by reference in its entirety. Once activated, the sensor 20 can be configured to take measurements continuously, periodically, or at predetermined intervals.

In some embodiments, a single sensor 20 may be employed to simultaneously sense both the atrial and ventricular mechanical activity within the heart (block 62), and then provide a single mechanical signal (64) to the pulse generator 16 that is then analyzed by the algorithm 50 to determine the hemodynamic status of the heart. In other embodiments, the sensor 20 is configured to sense mechanical activity in only one of the right atria or right ventricle. An example pressure sensor capable of sensing such mechanical activity is described in U.S. Pat. No. 6,140,740 to Portal et al., entitled "Piezoelectric Transducer," the contents of which is incorporated herein by reference in its entirety. Other types of sensors capable of detecting mechanical activity within the heart can also be utilized. Other types of sensors suitable for use in sensing mechanical activity within the body can include, but are not limited to, accelerometers, motion sensors, flow sensors, and temperature sensors.

From the mechanical activity signals received from the sensor 20, the control algorithm 50 analyzes the sensed mechanical activity within the heart to confirm the presence of the event detected by the sensed electrical activity (block 66). In some embodiments, the sensed mechanical activity can also be utilized to discriminate between different types of events. If from the sensed electrical signal the control unit 48 detects the presence of a tachycardia event, for example, the sensed mechanical activity signal from the sensor 20 can be used to determine whether the tachycardia is hemodynamically unstable and requires treatment in the form of an electrical shock, or is hemodynamically stable and may require other alternative forms of therapy or treatment.

If the event detected within the heart is confirmed by mechanical activity sensed by the sensor 20, the pulse generator 16 may then determine whether therapy is indicated for the confirmed event. If it is determined that therapy is desired, the pulse generator 16 can then deliver an appropriate treatment to the patient (block 68). If, on the other hand, the event is not confirmed by the sensed mechanical activity, or if the control algorithm 50 determines that therapy is not desired, the algorithm 50 may store the event in memory and sense one or more additional electrical and/or mechanical activity readings (block 70). In some embodiments, for example, if an event is falsely identified from the sensed electrical activity, the pulse generator 16 can be configured to take one or more additional readings from the sensor 20 to determine whether the event is indicative of another problem. The ability to discern this information in real-time from the sensed mechanical activity potentially reduces the number of inappropriate shocks the patient receives, improving patient comfort and health and extending the battery life of the pulse generator 16. Complications that could result from long-term over shocking and other forms of aggressive treatment are also ameliorated based on the reduction in false positives confirmed from the sensed mechanical activity.

The methods described herein may be used in any number of applications where rhythm discrimination within the heart or at other locations within the body is desired. In some embodiments, and as discussed further herein, the methods may be used for monitoring atrial-ventricular mechanical synchrony during an arrhythmia episode, distinguishing between symptomatic tachycardias and asymptomatic tachycardias, providing hemodynamic stability and perfusion information of the heart, as well as other information. Other heart-related applications where rhythm discrimination may be useful include, but are not limited to, CRT optimization, rate responsive pacing for bradycardia applications, ischemia detection, and drug titration applications. Other treatment locations within the body may also benefit from such rhythm discrimination. In one alternative embodiment, for example, such rhythm discrimination can be used to detect the presence of blood clots within a blood vessel such as in the coronary arteries.

Figure 3:
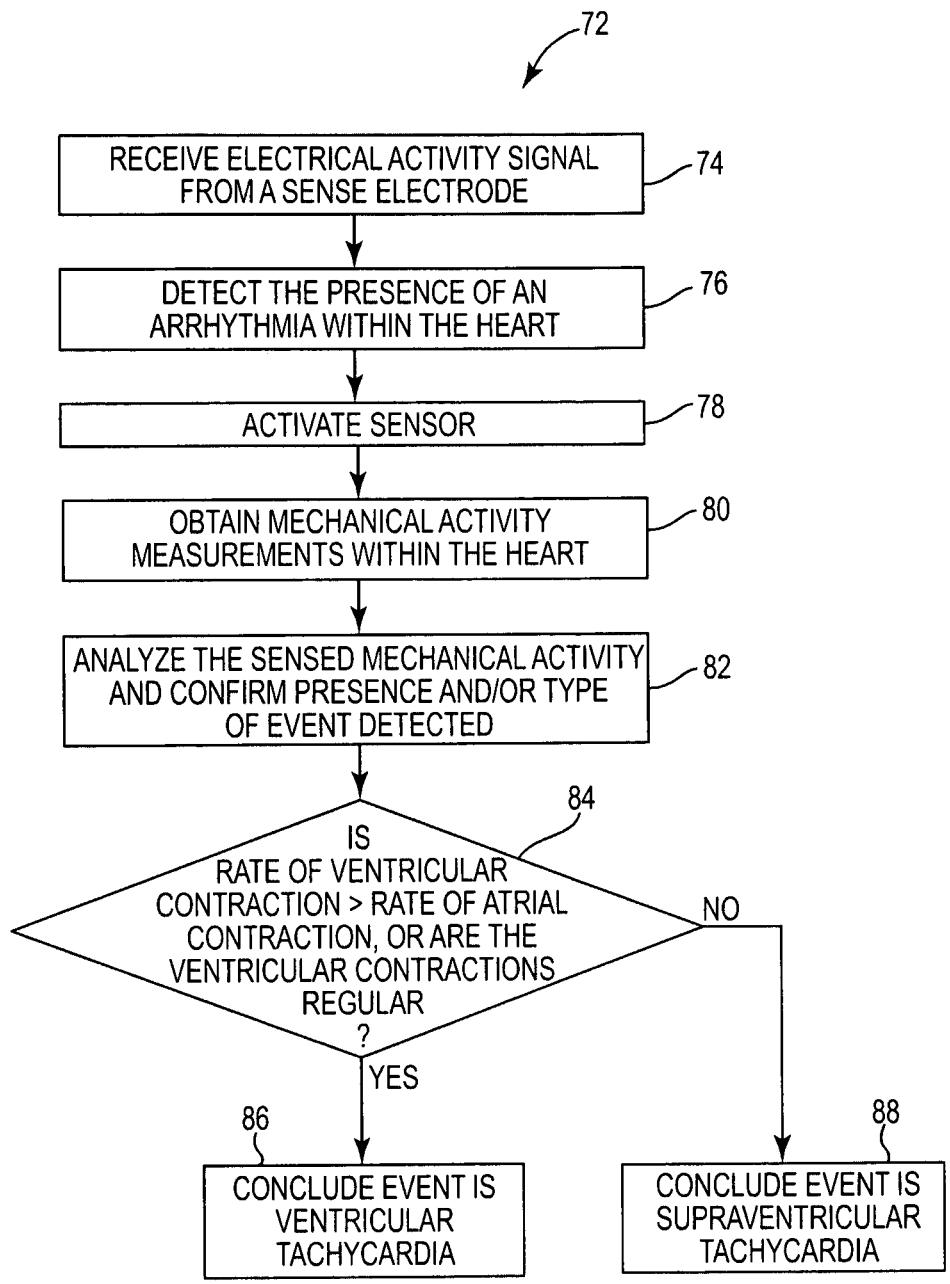
FIG. 3 is a flow chart showing an illustrative method of monitoring atrial-ventricular mechanical synchrony within the heart using sensed hemodynamic signals.

FIG. 3 is a flow chart showing an illustrative method 72 of monitoring atrial-ventricular (A/V) mechanical synchrony within the heart using sensed hemodynamic signals. In the embodiment of FIG. 3, the method 72 begins at block 74 with the step of receiving an electrical signal from a sense electrode implanted in or near the heart and detecting the presence of an arrhythmia event of the heart. In certain embodiments, the electrical signals can be received from a sense electrode inserted at or near the sinoatrial (SA) node of the heart. In addition, or in lieu, the electrical signals can be obtained from other locations in or near the heart such as in the right ventricle or the main pulmonary artery.

The electrical activity signals received from the sense electrodes can be fed to the control unit algorithm 50, which then analyzes these signals to detect the presence of an arrhythmia (block 76). For example, if the algorithm 50 determines that the patient's heart rate exceeds some predetermined level (e.g., 120 bpm) for a predetermined period of time (e.g., 5 seconds), the control unit 48 may conclude that the event is tachycardia.

Once a suspected event is detected, the sensor 20 may then be activated (block 78) and tasked to take measurements of the mechanical activity within the heart to confirm the presence of the event and/or to ascertain more information about the particular event (block 80). In some embodiments, for example, the pulse generator 16 sends a signal to a pressure sensor located within a pulmonary artery, causing the pressure sensor to begin taking pressure readings within the artery.

Based on the mechanical activity signals received from the sensor, the algorithm 50 analyzes (block 82) the sensed mechanical activity within the heart to confirm the presence of the event. In some embodiments, analysis of the mechanical activity signals includes the step (block 84) of comparing the right atrial and right ventricular contraction rates during an arrhythmia episode in order to verify the type of arrhythmia event occurring. If, for example, the ventricle contracts at a faster rate than the atrium for a certain number of cycles over a predetermined time period (e.g., greater than 10 cycles per minute), or, if the intervals between the ventricular contractions are regular, the algorithm 50 may conclude that the event is ventricular tachycardia (block 86). If the ventricle does not contract at a faster rate than the atrium over a predetermined time, or if the intervals between ventricular contractions are irregular, the algorithm 50 may conclude that the detected event is supraventricular tachycardia (block 88).

Depending on the type of arrhythmia detected, the pulse generator 16 may then deliver an appropriate treatment to the patient. For example, if the detected event is ventricular tachycardia, the pulse generator 16 can deliver an electric shock to the patient in the form of electrical cardioversion (e.g., synchronized cardioversion). If the detected event is supraventricular tachycardia, the pulse generator 16 can deliver an alternative form of therapy such as rate responsive pacing or drug titration. The type of therapy or treatment provided will often depend on the type of event detected, the frequency of the event, as well as other factors.

If the suspected event is not confirmed by the sensed mechanical activity, the algorithm 50 may store the event in memory and sense one or more additional electrical and/or mechanical activity readings. For example, if a suspected ventricular tachycardia event is falsely identified from the sensed electrical activity, the pulse generator 16 can be configured to ascertain one or more additional readings from the sensor 20 to determine whether the event is indicative of another problem.

Figure 4:
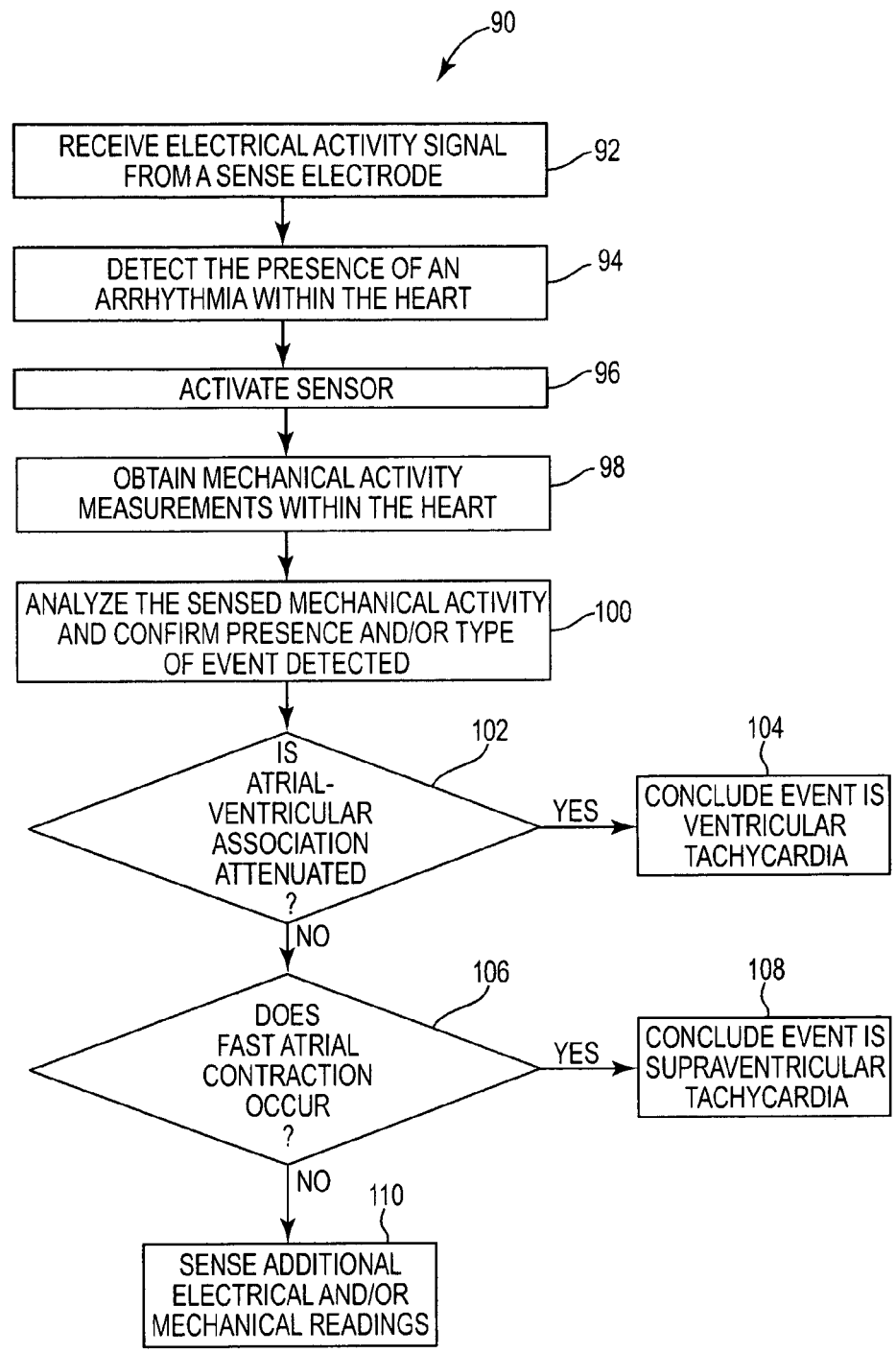
FIG. 4 is a flow chart showing another illustrative method of monitoring atrial-ventricular mechanical synchrony within the heart using sensed hemodynamic signals.

FIG. 4 is a flow chart showing another illustrative method 90 of monitoring atrial-ventricular mechanical synchrony within the heart using sensed hemodynamic signals. The method 90 of FIG. 4 is similar to that described with respect to FIG. 3, beginning at block 92 with the step of receiving an electrical activity signal from a sense electrode implanted in or near the heart. The electrical activity signals received from the implanted sense electrodes can be fed to the algorithm 50 for the control unit 48, which then analyzes the electrical activity signals to detect the presence of an arrhythmia (block 94) such as, for example, tachycardia.

Once a suspected event is detected, the sensor 20 may then be activated (block 96) and tasked to take measurements of the mechanical activity within the heart to confirm the presence of the event and/or to ascertain more information about the particular event (block 98). In some embodiments, for example, the pulse generator 16 sends a signal to a pressure sensor located within a pulmonary artery, causing the pressure sensor to take pressure readings within the artery.

Based on the mechanical activity signals received from the sensor, the algorithm 50 is configured to analyze (block 100) the sensed mechanical activity within the heart to confirm the presence of the event. In the illustrative embodiment of FIG. 4, analysis of the mechanical activity signals from the sensor 20 includes the step (block 102) of comparing the atrium-ventricle (AN) mechanical delay during the arrhythmia episode in order to verify the type of arrhythmia occurring. If, for example, the atrial-ventricular association is attenuated (block 102) such that there is an atrial-ventricular dissociation and the ventricular mechanical signal occurs before the atrial event, the algorithm 50 may conclude that the detected event is a ventricular tachycardia event (block 104). Conversely, if a fast atrial contraction occurs while a relatively maintained or constant AV association is present (block 106), the algorithm 50 may conclude that the detected event is a supraventricular tachycardia event (block 108). If the suspected event is not confirmed by the sensed mechanical activity, the algorithm 50 may store the event in memory and sense one or more additional electrical and/or mechanical activity readings to determine whether the event is indicative of another problem (block 110).

Figure 5A:
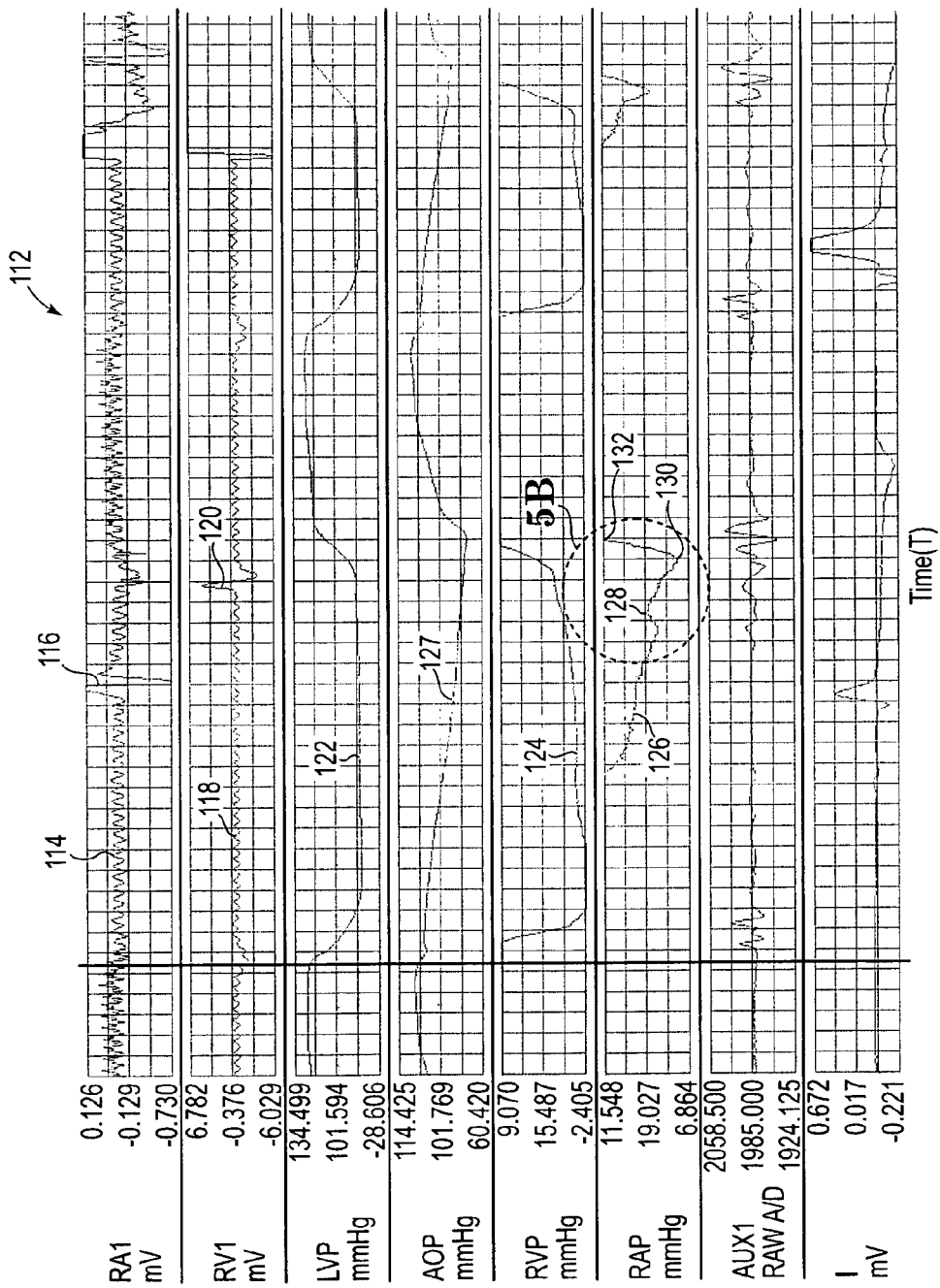
FIGS. 5A-5B include a graphical readout showing several illustrative electrical and mechanical readings sensed within a patient during an arrhythmia event.
Figure 5B:
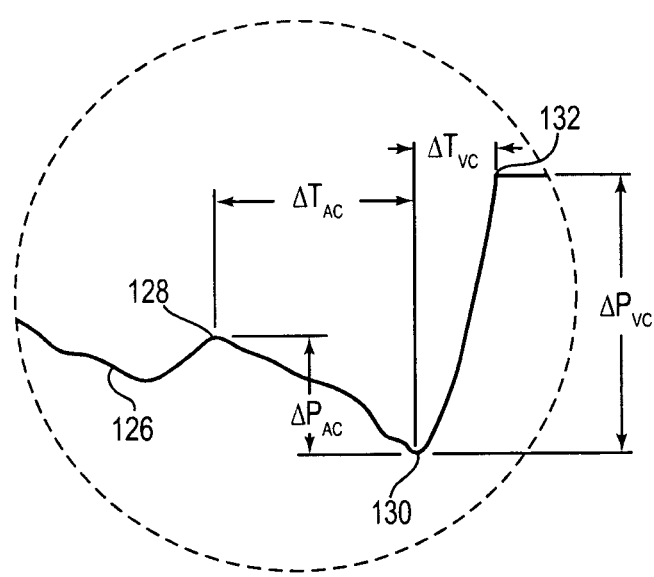

FIGS. 5A-5B include a graphical readout 112 showing exemplary electrical and mechanical readings sensed within a patient during an arrhythmia event. The readout 112 may represent, for example, a number of ECG or EGM electrical activity output signals received from electrodes implanted within the right atrium and right ventricle of the heart, and various mechanical activity output signals received from pressure sensors implanted in the left ventricle, right ventricle, and right atrium of the heart.

As shown in a first electrical output waveform 114 in FIG. 5A, which represents a voltage signal output (in mV) from an electrode implanted within the right atrium of the heart, the beginning of an arrhythmic event within the heart can be seen at point 116 along the waveform 114, which shows a rapid increase in voltage indicating a possible arrhythmic episode such as ventricular tachycardia or supraventricular tachycardia. The rapid increase in voltage at point 116 represents the electrical depolarization occurring within the heart. The occurrence of the event can be further seen with respect to a second electrical output waveform 118 in FIG. 5A, which represents a voltage signal output (in mV) from a second electrode implanted within the right ventricle of the heart. In the second output waveform 118 produced by the right ventricle sensor, the beginning of the event can be seen at point 120, which is delayed from point 116 on the first output waveform 114 due to the inherent signal delay from the sinus (SA) node to the atrioventricular (AV) node.

The graphical readout 112 further illustrates the mechanical activity occurring at various locations within the heart. A first mechanical activity output waveform 122, for example, represents the mechanical pressure (mmHg) from a pressure sensor implanted within the left ventricle. A second mechanical activity output waveform 124 represents the mechanical pressure (mmHg) from a pressure sensor implanted within the right ventricle. A third mechanical activity output waveform 126, in turn, represents the mechanical pressure (mmHg) from a pressure sensor implanted within a pulmonary artery. A fourth mechanical output waveform 127 represents the aortic pressure (mmHg) within the heart.

As can be seen from the pulmonary artery output waveform 126, the pulmonary artery pressure drops synchronously with the atrial contraction of the heart. As sensed from a single pressure sensor in the pulmonary artery, this contraction can be seen at a first point 128 along the waveform 126, which shows the timing association of the atrial contraction relative to the electrical signal at point 116 in waveform 114. At point 128, the pressure within the pulmonary artery increases slightly due to the atrial contraction, and then decreases until it reaches a second point 130, which indicates the beginning of the ventricular contraction.

As further shown in an exploded view of the mechanical activity output waveform 126 in FIG. 5B, the difference in time $\Delta T_{AC}$ between points 128 and 130 represents the duration in which atrial contraction of the heart occurs. The difference in pressure $\Delta P_{AC}$ between points 128 and 130 represents the change in pressure occurring over this time period. From this information, an atrial contraction rate (ACR) can be determined generally by the following expression:

$$\text{Atrial contraction rate (ACR)} = \Delta P_{AC}/\Delta T_{AC}.$$

The rate of ventricular contraction can also be ascertained from the pulmonary artery pressure sensor signal in a similar manner by comparing the rate at which the ventricular contraction occurs at the point in which the ventricular pressure increases. This period of contraction in the ventricle can be seen between points 130 and 132 on the output waveform 126. As with the atrial contraction rate, the ventricular contraction rate (VCR) can be determined from the change in pressure $\Delta P_{VC}$ from points 130 to 132 divided by the change in time $\Delta T_{VC}$ between points 130 and 132. This can be seen from the following expression:

$$\text{Ventricular contraction rate (VCR)} = \Delta P_{VC}/\Delta T_{VC}.$$

In some embodiments, the step (block 84) in FIG. 3 of comparing the right atrial and right ventricular contraction rates during an arrhythmia episode includes the step of computing the atrial contraction rate (ACR) and ventricular contraction rate (VCR) from the above expressions, and then comparing these mechanical contraction rates to determine the type of arrhythmia event initially detected from the electrical output waveform 114. If, for example, the ventricular contraction rate (VCR) is greater than the atrial contraction rate (ACR), the algorithm 50 for the control unit 48 may conclude that the event is ventricular tachycardia (block 86). If the ventricle does not contract a faster rate than the atrium, the algorithm 50 may conclude that the detected event is supraventricular tachycardia (block 88).

A comparison of the mechanical delays occurring during the arrhythmic event can also be used to determine the type of arrhythmia detected from the electrical output waveform 114. In the method 90 described above with respect to FIG. 4, for example, the steps 102,106 of comparing the atrium-ventricular (A/V) mechanical delay during the arrhythmia episode can include computing the delay at which atrial contraction begins at point 128 with the time at which ventricular contraction begins at point 130 on the output waveform 126. Using either of the electrical output waveforms 114, 118, the algorithm 50 may then compute an atrium-ventricular (A/V) delay during the event to determine the type of arrhythmia occurring. If, for example, the relative delays between when atrial contraction begins and ventricular contraction begins is relatively short, the algorithm 50 may conclude that the detected event is a ventricular tachycardia event (block 104). Conversely, if a fast atrial contraction occurs while a relatively maintained or constant AV association is present, the algorithm 50 may conclude that the detected event is a supraventricular tachycardia event (block 108).

In some embodiments, the algorithm 50 is configured to monitor atrial and/or ventricular electromechanical activity to determine the presence of an event within the patient's heart. In one embodiment, for example, the algorithm 50 may compare the time at which the arrhythmia occurs, as indicated generally at point 116 on the electrical output waveform 114, with the timing of the atrial and ventricular contractions sensed by the pulmonary artery sensor. Such monitoring of the electromechanical activity can be used, for example, to indicate the presence of other events and/or activity occurring within the patient's body. In some embodiments, for example, the monitoring of such electromechanical activity can be used to detect an electrolyte imbalance within the patient or to detect the occurrence of heart decompensation or heart failure.

Figure 6:
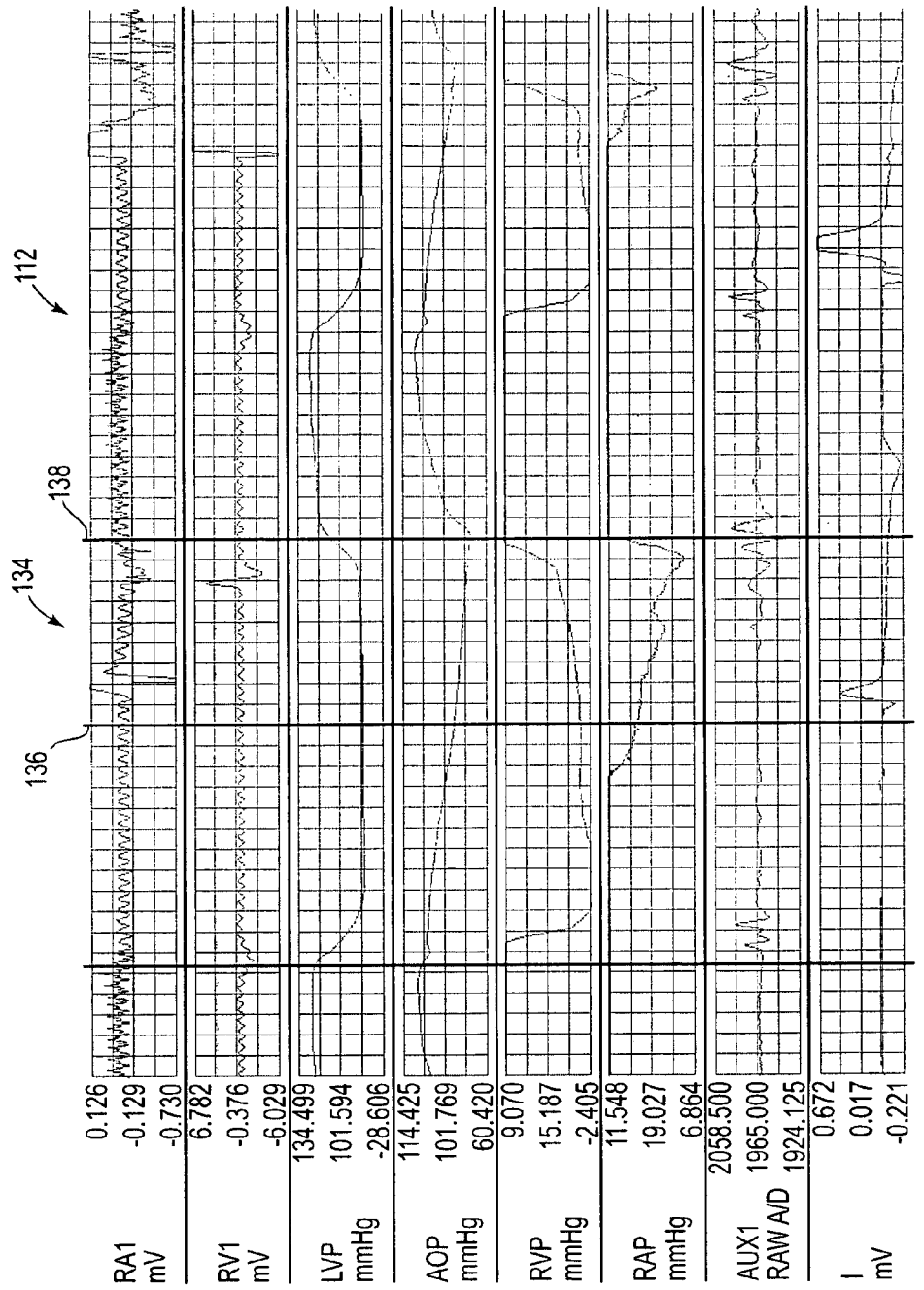
FIG. 6 is another view of the graphical readout of FIG. 5A showing an open atrial mechanical window placed on a fiducial point of the readout.

To increase the sensitivity of the mechanical sensing, and in some embodiments, the algorithm 50 may use an open atrial mechanical window to isolate a sequence of events for analysis. As further shown in FIG. 6, for example, an open atrial mechanical window 134 can be placed at a fiducial point 136 on the readout 112 such as at the end of systole or atrial EGM. The window 134 can be configured to close or terminate at point 138 after a predetermined period of time (e.g., 75 ms, 100 ms, 125 ms, etc.) has elapsed and/or until at such point a particular event has been detected. In some embodiments, the algorithm 50 may select a window 134 for analysis based on the detection of a previous event or based on a suspected event.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of performing rhythm discrimination within the body of a patient, comprising:
   receiving an electrical activity signal from an electrode located within or adjacent to the heart;
   detecting an event of the heart based at least in part on the electrical activity signal;
   receiving a physiological mechanical activity signal from a pressure sensor located in a pulmonary artery of the patient, the pressure sensor configured to sense both atrial contraction and ventricular contraction within the heart;
   analyzing the physiological mechanical activity signal received from the pressure sensor to determine an atrial contraction parameter and a ventricular contraction parameter associated with the heart; and
   confirming the event by comparing the atrial contraction parameter against the ventricular contraction parameter, wherein comparing the atrial contraction parameter against the ventricular contraction parameter comprises determining, based on the physiological mechanical activity signal, an atrium-ventricle (A/V) mechanical delay, and determining a type of the event based on the A/V mechanical delay.

2. The method of claim 1, further comprising providing therapy to the patient based at least in part on the type of event confirmed.

3. The method of claim 1, further comprising activating the sensor within the body upon the detection of the event from the electrical activity signal.

4. The method of claim 3, wherein activating the sensor includes sending a wake-up signal to the sensor causing the sensor to switch between a first state and a second state.

5. The method of claim 1, wherein analyzing the physiological mechanical activity signal received from the sensor includes comparing a right atrial contraction rate to a right ventricular contraction rate.

6. The method of claim 1, wherein confirming the event includes:
   determining that the event is a ventricular tachycardia event when an A/V association is attenuated; and
   determining that the event is a supraventricular tachycardia event when a fast atrial contraction occurs while a substantially constant A/V association is present.

7. The method of claim 1, further comprising analyzing electromechanical activity within the heart using both the physiological mechanical activity signal and the electrical activity signal.

8. The method of claim 1, further comprising applying an open atrial mechanical window to the sensed physiological mechanical and electrical activity signals.

9. The method of claim 1, wherein analyzing the physiological mechanical activity signal and confirming the event are performed by an implantable medical device.

10. A method of performing rhythm discrimination within the body of a patient, comprising:
    providing an implantable medical device including a control unit adapted to run an algorithm for detecting arrhythmia events within the heart;
    receiving an electrical activity signal from an electrode located within or adjacent to the heart;
    detecting an arrhythmia event of the heart based at least in part on the electrical activity signal;
    responsive to detecting the arrhythmia event, prompting a pressure sensor located within a pulmonary artery of the patient to activate and sense one or more physiological pressure measurements associated with the atrial contraction and ventricular contraction of the heart;

determining, based at least in part on the sensed physiological pressure measurements received from the sensor, an atrial contraction rate and a ventricular contraction rate;

confirming the event by comparing the atrial contraction rate against the ventricular contraction rate, wherein confirming the event further comprises determining, based on the sensed physiological pressure measurements, an atrium-ventricle (A/V) mechanical delay, and determining a type of the event based on the A/V mechanical delay; and providing a therapy to the patient in response to confirming the event.

11. The method of claim 10, where confirming the event includes:

determining that the event is a ventricular tachycardia event when an A/V association is attenuated; and determining that the event is a supraventricular tachycardia event when a fast atrial contraction occurs while a substantially constant A/V association is present.

12. The method of claim 10, further comprising analyzing electromechanical activity within the heart using both the sensed physiological pressure measurements and the electrical activity signal.

13. The method of claim 10, further comprising applying an open atrial mechanical window to the sensed electrical signals and sensed physiological pressure measurements.

14. A system for performing rhythm discrimination within the body of a patient, comprising:

an electrode configured to sense electrical activity of the heart and to provide an electrical activity signal based on the sensed electrical activity;

a mechanical pressure sensor adapted to be located in a pulmonary artery, the sensor configured to sense a physiological mechanical activity signal comprising both atrial and ventricular contraction of the heart; and an implantable medical device in communication with the electrode and the sensor, the implantable medical device configured to:

detect an arrhythmia event of the heart based at least in part on the electrical activity signal received from the electrode;

analyze the physiological mechanical activity signal received from the sensor to determine an atrial contraction parameter and a ventricular contraction parameter associated with the heart;

confirm the arrhythmia event by comparing the atrial contraction parameter against the ventricular contraction parameter to determine an atrium-ventricle (A/V) mechanical delay;

determine a type of the event based on the A/V mechanical delay;

provide therapy to the patient based at least in part on the comparison of the atrial contraction parameter against the ventricular contraction parameter, the A/V mechanical delay, and the electrical activity signal received from the electrode.

15. The system of claim 14, wherein the implantable medical device is a pulse generator.

* * * * *